United States Patent [19]

Tahara

[11] Patent Number: 5,225,579
[45] Date of Patent: Jul. 6, 1993

[54] METHOD OF MANUFACTURING VITAMIN D2, VITAMIN D3, ACTIVATED TYPE VITAMIN D2, ACTIVATED TYPE VITAMIN D3, AND THEIR DERIVATIVES

[75] Inventor: Yuji Tahara, Sapporo, Japan

[73] Assignee: Hoxan Corporation, Hokkaido, Japan

[21] Appl. No.: 873,887

[22] Filed: Apr. 24, 1992

Related U.S. Application Data

[63] Continuation of Ser. No. 571,534, Aug. 29, 1990, abandoned.

[30] Foreign Application Priority Data

Mar. 16, 1988 [JP] Japan ................... 63-62517

[51] Int. Cl.$^5$ .................. C09J 9/00; C07C 401/00
[52] U.S. Cl. .................... 552/653; 568/817; 568/822; 568/828; 568/838
[58] Field of Search ............. 514/167; 568/828, 445, 568/817, 822, 824, 838; 552/653

[56] References Cited

U.S. PATENT DOCUMENTS

| | | | |
|---|---|---|---|
| 4,424,161 | 1/1984 | Holick | 552/653 |
| 4,448,721 | 5/1984 | DeLuca et al. | 568/817 |
| 4,847,012 | 7/1989 | DeLuca et al. | 552/653 |

FOREIGN PATENT DOCUMENTS

| | | | |
|---|---|---|---|
| 5828876 | 11/1979 | Japan | 552/653 |
| 59-45673 | 8/1983 | Japan | 552/653 |
| 59-45674 | 8/1983 | Japan | 552/653 |
| 59-45675 | 8/1983 | Japan | 552/653 |
| 59-176250 | 10/1984 | Japan | 552/653 |
| 158158 | 8/1954 | United Kingdom | |
| 2217716 | 11/1989 | United Kingdom | 568/445 |

OTHER PUBLICATIONS

Baggiolini et al., "Sterospecific Synthesis of the Lythgoe's Ring A Aldehyde for the Preparation ... *Tetrahedron Letters*", 28(19): 2095-2098 (1987).

Tanaka et al., "1α, 25-Dihydroxycholecalciferol and a Human Myeloid Leukaemia Cell Line", *Biochem. J.*, 204:713-719 (1982).

DeLuca et al., "Metabolism and Mechanism of Action of Vitamin D[1]", *Ann. Rev. Biochem.*, 45: 631 (1976).

Manolagas et al., "1,25-Dihydroxyvitamin $D_3$ Receptor-like Macromolecule in Rat Osteogenic Sarcoma Cell Lines", *J. Bio. Chem.*, 255(10): 4414-4417 (1980).

Abe, *Vitamin*, 59: 418 (1985).

Kaneko, "1α-Hydroxyvitamin $D_3$ ... ", *Org. Synth. Chem.* 33: 75 (1975).

Baggiolini et al., "Sterocontrolled Total Synthesis of 1α, 25-Dihydroxycholecalciferol[1]. . . ", *J. Org. Chem.* 51: 3098-3108 (1986).

Castedo et al., "An improved Synthesis of 1α,25-Dihydroxyvitamin D A Snythons[1]", *Tetrahedron Letters*, 28(19): 2099-2102 (1987).

Okamura et al., "Studies on a Convergent Route to Side-Chain Analogues of Vitamin D: ... ", *J. Org. Chem.*, 48: 1414-1417 (1983).

Mazur et al., "The Vitamin D-3,5-Cyclovitamin D Rearrangement", *J. Am. Chem. Soc.*, 97: 6249 (1979).

DeLuca et al., "Cellular and Subcellular Localization of 1,25-$(OH)_2$vitamin $D_3$ in Rat Kidney ... " *Proc. Natl. Acad. Sci. USA*, 77(2): 1149-1153 (1980).

Abe et al., "Differentiation of Mouse Myeloid Leukoid Leukemia Cells Induced by 1α,25-dihydroxyvitamin $D_3$", *Proc. Natl. Acad. Sci. USA*, 78(8) 4990-4994 (1981).

Morzycki et al. "Reprint Journal of Organic Chemistry" (1984) 49, 2148.

*Primary Examiner*—Werren B. Lone
*Attorney, Agent, or Firm*—Foley & Lardner

[57] ABSTRACT

There is provided a method with which vitamin $D_2$, vitamin $D_3$, activated type vitamin $D_2$, activated type vitamin $D_3$ and their derivatives are prepared from 7,8-dihyroxy vitamin $D_2$, $D_3$ or any of their derivatives by means of a reducing elimination technique involving as cyclic orthoester of a 7,8-dihydroxy compound or a thiocarbonate compound as an intermediate compound or an elimination technique utilizing a reducing metal such as titanium. The method according to the invention ensures a practical and simple synthetic process and a high yeild as compared with any existing methods for manufacturing these chemicals.

7 Claims, No Drawings

METHOD OF MANUFACTURING VITAMIN D2, VITAMIN D3, ACTIVATED TYPE VITAMIN D2, ACTIVATED TYPE VITAMIN D3, AND THEIR DERIVATIVES

This application is a continuation of application Ser. No. 07/571,534, filed Aug. 29, 1990, now abandoned.

FIELD OF THE INVENTION

This invention relates to a method of manufacturing vitamin $D_2$, vitamin $D_2$, activated type vitamin $D_2$, activated type vitamin $D_3$ and their derivatives from 7,8-dihydroxy vitamin $D_2$, 7,8-dihydroxy vitamin $D_3$ and their derivatives.

BACKGROUND OF THE INVENTION

There has been a remarkable development of study of vitamin D since 1958 when 25-hydroxy vitamin $D_3$ was found as an activated metabolite of vitamin $D_3$ and more extensively since 1971 when 1α,25-dihydroxy vitamin $D_3$ which is by far the most activated substance of all the known metabolites of vitamin $D_3$ was discovered. (See the following reference papers.)

Reference Paper 1: H. F. DeLuca et al., Ann. Rev. Biochem., vol.45, p.631, 1976

Reference Paper 2: H. F. DeLuca, Nutr. Rev., vol.37, p.161, 1979

Since then extensive reseaches have been done in the fields of biochemistry, organic chemistry, and medicine through cooperation of researchers of these and other research areas. As a result of the research efforts, 1α, 25-dihydroxy vitamin $D_3$ which is an activated type vitamin $D_3$ and its homologue 1α, 25-hydroxy vitamin $D_3$ were developed as medicines for kidney diseases, bone diseases and thyroidal disorders. (See the following reference papers.)

Reference Paper 3: D. E. M. Lawson, "vitamin D", Academic Press, Inc., New York, 1978

Reference Paper 4: A. W. Norman, "Vitamin D, The Calcium Homeostasis Steroid Hormon", Academic Press, Inc., New York, 1979

It has been known for some time that 1α, 25-dihydroxy vitamin $D_3$ is particularly effective for small intestine and bone and more recently there was a report evidencing that kidney, pancreas, pituitary body, thymus, thyroid, skin, mammary gland, lymphocyte and many other tissues and organs have receptors for the chemical. (See Reference Paper 5 below.) Likewise, it has also been proved that various tumorous cells such as malignant melanoma celss (see Reference Paper 6 below), breast cancer cells (see Reference Paper 7 below), osteogenic sarcoma cells (see Reference Paper 8 below) and myeloid leukemia cells (see Reference Paper 9 below) have receptors.

Reference Paper 5: H. F. DeLuca et al., Proc. Natl. Acas. Sci. USA, vol.77, p.1149, 1980

Reference Paper 6: K. Colston et al., Endocrinology, vol. 108, p.1083, 1981

Reference Paper 7: H. F. Freake et al., Biochem.Biophys. Res.Commun., vol.101, p.1131, 1981

Reference Paper 8: S. C. Mnolagas et al., J.Biol.Chem., vol.255, p.4414, 1980

Reference Paper 9: T. Suda et al., Biochem.J., vol.204, p.713, 1982

Particularly the fact that 1α, 25-dihydroxy vitamin $D_3$ suppresses proliferation of myeloid leukemia cells and accelerates differentiation of cells (see Reference Paper 10 below) and that there is a certain relationship between activated type vitamin D and the immune system of the body suggests potential and encouraging applications of the chemical (see Reference Paper 11 below).

Reference Paper 10: T. Suda et al., Proc.Natl,Acad.Sci., USA, vol.78, p.4990

Reference Paper 11: E. Abe, Vitamin, vol.59, p.418, 1985

Since the 1α-hydroxy component of activated type vitamin D and its various derivatives is considered to play a vital and fundamental role in the physiological effects of these chemicals, many of laboratories and research institutes all over the world have been concentrating their efforts on the study of the component and consequently a number of achievements have been reported in the research field. Some of the examples of the achievements of the researches include, 1) a photochemical method of obtaining desired vitamin D derivaties in which 1α-hydroxidated steroid is synthesized in the first place and then it is converted to the corresponding 1α-hydroxy-5,7-dienesterol derivative which is used as material for the vitamin derivative, Reference Paper 12: C. Kaneko, Organic Synthetic Chemistry, vol.33, p.75, 1975, etc.

2) a method with which a vitamin D derivative is converted to a 3,5-cyclovitamin derivate and then combined with allylic acid at position C(1), the product being converted again to obtain the desired vitamin D derivative, Reference Paper 13: H. F. DeLuca et al., J. Org. Chem., vol.45, p.3253, 1980 etc.

3) a method with which vitamin D is temporarily converted to transvitamin D, which is combined with allylic acid at position C(1), the product being photochemically reconverted to vitamin D and Reference Paper 14: R. H. Hesse et al., J. Org. Chem., vol.51, p.1635, p.4819, 1986 etc.

4) a method with which a fragment corresponding to an A-ring portion and having a hydroxyl group at position C(1) is synthesized with a view to total synthesis and then combined with a fragment that corresponds to a D-ring portion to obtain the aimed compound.

Reference Paper 15: W. H. Okamura et al., Tetrahedron Letters, vol.28, p.2095, 1987

Reference Paper 16: E. G. Baggiolini et al., J.Org.-Chem., vol.51, p.3098, 1986

Reference Paper 17: L. Castedo et al., Tetrahedron Letters, vol. 28, p. 2099, 1987 etc.

Of the above cited methods, the method 1) is most popularly used as it is a relatively practical one, although it comprises a number of steps required to introduce a hydroxyl group to position 1α and its stereo- and positional selectivity is not very good, making the overall process rather inefficient as a number of steps are further required to obtain the aimed final vitamin D derivative by means of conversion. On the other hand, the method 2) allows use of any known process for conversion from vitamin D to 3,5-cyclovitamin D with a high yield (see the paper below).

Reference Paper 18: Y. Mazur et al., J. Am. Chem. Soc., vol.97, p.6249, 1979

The reaction with allylic acid of the method 2) above has a high stereoselectivity although it can not be conducted with a high yield as oxo compounds are brought forth at position C(1) as by-product at a significant level. Moreover, the method (b) is accompanied by other problems such as the fact that by-products including transvitamin D which are not easily separable from the aimed 1α-hydroxy vitamin D are produced in the solvolysis of the 1α-hydroxy compound of the product.

The method 3) can not be conducted without problems either because it entails a low yield at the stage of oxidzation or because a photochemical process is required for conversion of the oxidized compound into vitamin D, although it has a high yield of conversion from vitamin D to transvitamin D.

Finally, the method 4) is practically not a satisfactory one in view of the fact that it requires a number of steps throughout the whole process.

As is apparent from the above description, any existing and prevalent methods are not satisfactory in view of practical applications and development of more effective and efficient methods is desired.

The inventor of the present invention has, with due regard to these problems, carried out an extensive research for development of an effective synthetic method for producing significant intermediate compounds that can be combined with allylic acid at position C(1) for production of vitamin D and finally come to develop an effective and efficient method which is based on a concept and procedures completely different from those of any existing methods and in which aimed vitamin $D_2$, vitamin $D_3$, activated type vitamin $D_2$, activated type vitamin $D_3$ or any of their derivatives is obtained from 7,8-dihydroxy vitamin $D_2$, $D_3$ or any of their derivatives by means of a reducing elimination technique involving a cyclic ortho-ester or a thiocarbonate of a 7,8-dihydroxy compound as an intermidiate compound or an elimination technique utilizing a reducing metal such as titanium.

DISCLOSURE OF THE INVENTION

The object of the invention is achieve by providing a method of manufacturing vitamin $D_2$, vitamin $D_3$, activated type vitamin $D_2$, activated type vitamin $D_3$ and their derivatives expressed by formula [II] below

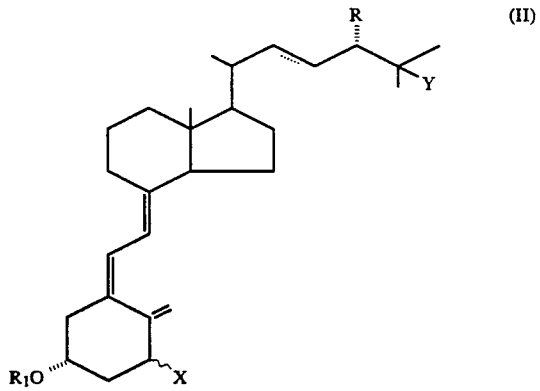

(where
R represents a hydrogen atom and the dotted line along a side chain represents an additional C—C bonding; or
R represents a methyl group and the dotted line along a side chain represents an additional C—C bonding; whichever the case may be,
$R_1$, $R_2$ and $R_3$ represent not necessarily identically a hydrogen atom or a hydroxy protecting group; and
X and Y represent a hydrogen atom, a hydroxy group or its derivative)

wherein 7,8-dihydroxy vitamin $D_2$ or $D_3$ or any of their derivatives expressed by formula [I] below

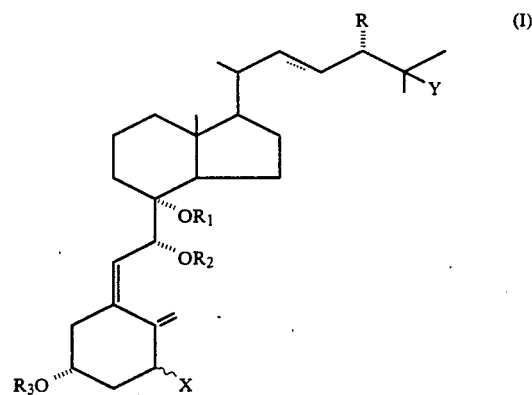

(where
R represents a hydrogen atom and the dotted line along a side chain represents an additional C—C bonding; or
R represents a methyl group and the dotted line along a side chain represents an additional C—C bonding; whichever the case may be,
$R_1$, $R_2$ and $R_3$ represent not necessarily identically a hydrogen atom or a hydroxy protecting group; and
X and Y represent a hydrogen atom, a hydroxy group or its derivative)

is subjected to a reducing elimination reaction by way of a cyclic ortho-ester, its homologue or its thiocarbonate or an elimination reaction by means of a reducing metal such as titanium.

The method according to the invention can be used for effectively manufacturing the above cited chemical compounds on industrial basis as it produces a compound expressed by formula II from a compound of formula I by means of desorption reaction and is therefore theoretically and practically different from any known methods.

PREFERRED EMBODIMENTS OF THE INVENTION

Of the compounds which are used for the method of the invention and generally expressed by formula [1] above, the following ones are very popular.

One is 7,8-dihydroxy-7,8-dihydro vitamin $D_3$ ($R_1$, $R_2$, $R_3$, X and Y=H; without a dotted line along a side chain), 3β-O-(t-butyldimethylsilyl)-7,8-dihydroxy-7,8-dihydro vitamin $D_3$ ($R_1$, $R_2$, R, X and Y=H; $R_3$=Si—-BuMe; without a dotted line along a side chain) (see Reference Paper 19 below).

Reference Paper 19: W. H. Okamura et al., J. Org. Chem., vol.48, p.1414, 1983

Another comoupnd is 7,8-dihydroxy vitamin $D_2$ ($R_1$, $R_2$, $R_3$, X and Y=H; R=Me; with one or more one dotted lines along side chains) (see Reference Paper 20 below).

Reference Paper 20: Y. Wang et al., Acta. Chem. Sin., vol.24, p.126, 1958)

Still another compound is any of derivatives of 7,8,25-trihydroxy vitamin $D_3$ (R, X=H; $R_1$, $R_2$ and $R_3$=H or a hydroxy protecting group; Y=$OR_4$ where $R_4$=H or a hydroxy protecting group; without a dotted line along a side chain) (see Reference Paper 21 below).

Reference Paper 21: H. F. DeLuca et al., Japanese Patent Application No. 59-93130

Isolation of the desired chemical from the mixture of reaction products can be conducted very easily. In one known isolation process, the reaction product containing vitamin $D_2$, vitamin $D_3$ or any of their active type homologues is solved in toluene with an excessive amount of orthoethylformate and an amount of camphor sulfonic acid good for a catalyst and the mixture is stirred at room temperature to form a cyclic orthoester compound of the chemical. Then prior to isolation, the mixture is heated in a Dean-Stark apparatus for reflux and thereafter the solvent is removed from the mixture by distillation. The residue is refined by means of column chromatography to obtain pure vitamin $D_2$, vitamin $D_3$ or any of their derivatives at a high yield.

Now the present invention will be described in greater detail by way of examples. In the following description, vitamin D refers to vitamin $D_2$ and vitamin $D_3$ and the spectrum values represent those of vitamin $D_3$.

EXAMPLE 1

Preparation of 3β-O-(t-butyldimethylsilyl) vitamin D

A 100 mg of 3β-O-(t-butyldimethylsilyl)-7,8-dihydoxy-7,8-dihydro vitamin D and 100 mg of triethylorthoformate were dissolved in 20 ml of toluene and an amount of camphor sulfonic acid good for catalyst was added to the solution while it was being stirred at room temperature. The solution was further stirred for 30 minutes at the same temperature and then heated in a Dean-Stark apparatus for four hours for reflux. After completion of reaction, the solvent was removed by distillation and the residue was subjected to a silica gel column chromatography process (silica gel 1 g, solvent; n-hexane) to obtain 67 mg of vitamin D combined with 3β-O-(t-butyldimethylsilyl).

The chemical structure of the product was identified by comparing its IR and NMR spectrums with those of a specimen producted by directly combining vitamin D and t-butyldimethylsilyl.

The reaction formulas are shown below.

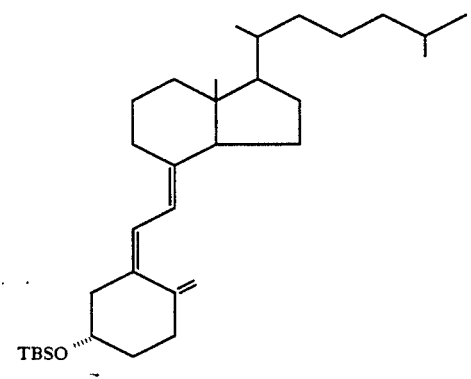

EXAMPLE 2

Preparation of 3β-(t-butyldimethyl-silyl) vitamin D

A 100 mg of 1β-acetoxy-3β-O-(t-butyldimethylsilyl)-7,8-dihydroxy-7,8-dihydro vitamin D and 100 mg of triethylortho-formate are dissolved in 20 ml of toluene with an amount of camphor sulfonic acid good for catalyst and the solution was heated for two hours in a Dean-Stark apparatus for reflux. After completion of reaction, the solvent was removed by distillation and the residue was subjected to a silica gel column chromatography process (silica gel 1 g, solvent; n-hexane) to obtain 50 mg of 1β-acetoxy-t-butyldimethylsilyl vitamin D.

IR spectrum: $\nu$max (CHCl$_3$) cm$^{-1}$: 1720

NMR spectrum: (CCl$_4$) δ: 0.10(6H,S), 0.57(3H,S), 0.87(9H,d,J=6 Hz), 0.93(9H,S), 2.10(3H,S), 3.55–4.10(1H,m), 4.87(1H,brs), 4.80–5.15(1H,m), 5.15(1H,m), 5.15(1H,brs), 5.85(1H,d,J=12 Hz), 6.23(1H,d,J=12 Hz)

mass spectrum (FD)m/e: 590(M$^-$), 589, 573, 498, 438, 378

The reaction forlumas are shown below.

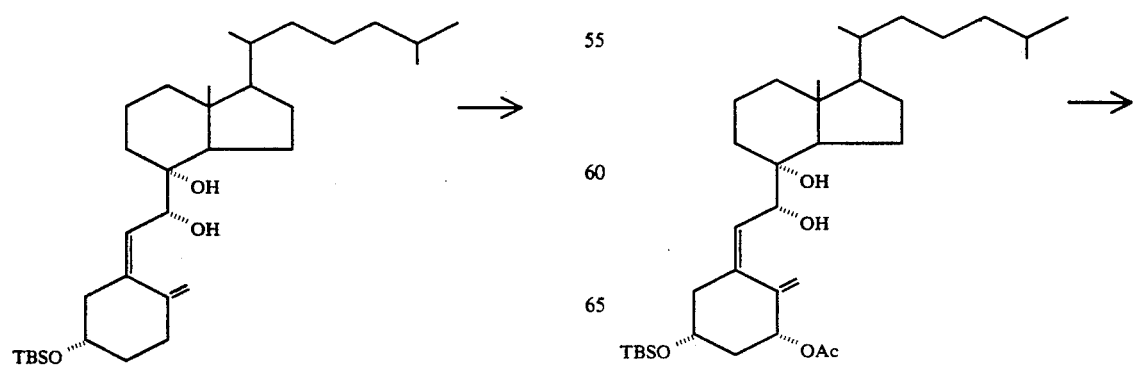

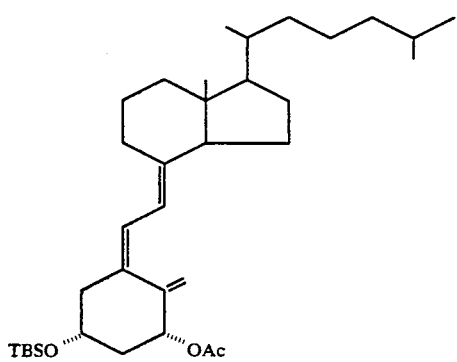

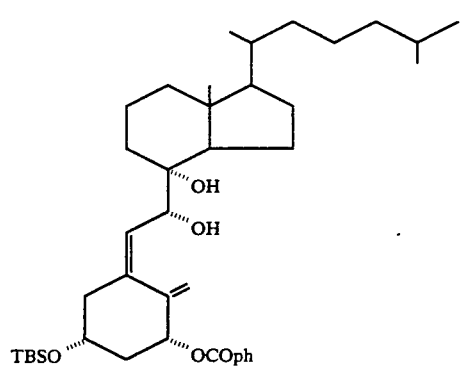

EXAMPLE 3

Preparation of
1β-benzoyloxy-3β-O-(t-butyldimethylsilyl)-7,8-dihydroxy-7,8-dihydro vitamin D A 200 mg of 3β-O-(t-butyldimethylsilyl)-7,8-dihydroxy-7,8-dihydro-1β-hydroxy vitamin D and 21 ml of pyridine were dissolved in 5 ml of dry methylene chloride with an amount of 4-dimethylaminopyrine for catalyst and 70 mg of benzoyl chloride was added to the solution while it was being stirred at 0° C. After completion of reaction, the solution was diluted with 30 ml of methylene chloride while it was being stirred at room temperature and then washed sequentially with water, 10% hydrochloric acid, saturated aqueous solution of sodium hydrogencarbonate and water. After drying the solution with sodium sulfate and removing the solvent by distillation, the residue was subjected to a silica gel chromatography process [silica gel 4 g, solvent; n-hexane-ethyl acetate (100:5 v/v)] to obtain 200 mg of 1β-benzoyloxy-3β-O-(t-butyldimethylsilyl)-7,8-dihydroxy-7,8-dihydro vitamin D.

IR spectrum: ν max (CHCl₃) cm⁻¹: 3550, 1710

NMR spectrum: (CCl₃) δ: 0.10(6H,S), 0.75(3H,S), 0.85(9H, d,J=6 Hz), 0.90(9H,S), 3.40–3.90(1H,m), 4.75(1H,d,J=10 Hz), 5.10(2H,brs), 5.10–5.30(1H,m), 5.70(1H,d,J=10 Hz), 7.30–7.60 (3H,m), 7.93–8.20(2H,m)

mass spectrum (FD)m/e: 652(M⁻), 635, 617, 595, 577, 560, 530, 513, 473, 442

The reaction formulas are shown below.

EXAMPLE 4

Preparation of 1β benzoyloxy-3β-O-(t-butyldimethylsilyl) vitamin D

A 100 mg of 1β-benzoyloxy-O-(t-butyldimethylsilyl)-7,8-dihydroxy-7,8-dihydro vitamin D and 100 mg of triethyl-orthoformate were dissolved in 20 ml of dry toluene with an amount of pyridinium-para-toluenesulfonate good for catalyst and the solution was heated in a Dean-Stark apparatus for ten minutes for reflux. After completion of reaction, the solvent was removed by distillation and the residue was subjected to a silica gel column chromatography process [silica gel 1 g, solvent; n-hexane-benzene (100:1 v/v)] to obtain 50 mg of 1β-benzoyloxy 3β-O-(t-butyldimethyl-silyl) vitamin D.

IR spectrum: ν max (CHCl₃) cm⁻¹: 1715

NMR spectrum: (CCl₄) δ: 0.10(6H,S), 0.55(3H,S), 0.88(9H, d,J=6 Hz), 0.90(9H,S), 3.60–4.20(1H,m), 4.93(1H,brs), 5.30 (1H,brs), 5.20–5.60(1H,m), 5.86(1H,d,J=12 Hz), 6.26(1H,d, J=12 Hz), 7.30–7.60(3H,m), 7.97–8.20(2H,m)

mass spectrum (FD)m/e: 6.18(M⁻), 496, 119

The reaction formulas are shown below.

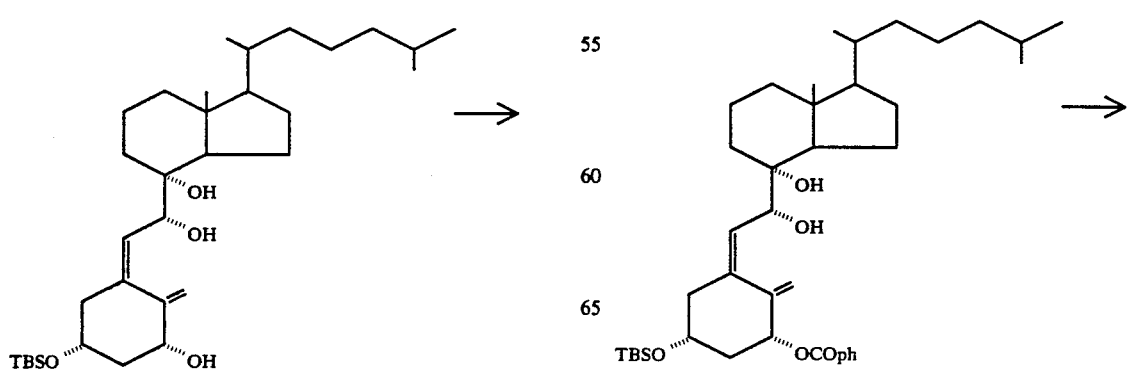

-continued

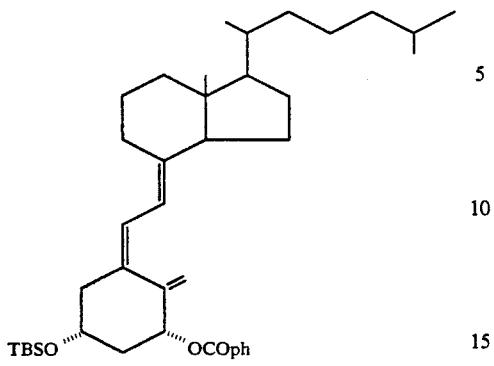

EXAMPLE 5

Preparation of 3β-O-(t-butyldimethylsilyl)-7,8-dihydroxy-7,8-dihydro-1β-methoxycarbonyloxy vitamin D A 100 mg of 3β-O-(t-butyldimethylsilyl)-7,8-dihydroxy-7,8-dihydro-1β-hydroxy vitamin D and 1 ml of pyridine are dissolved in 2 ml of dry methylene chloride with an amount of 4-dimethylaminopyridine good for catalyst and then 100 mg of methyl chlorocarbonate was added to the solution while it was being stirred at 0° C. The solution was further stirred for two hours at room temperature and diluted with 20 ml of methylene chloride. The diluted solution was washed sequentially with water, 10% hydrochloric acid, saturated aqueous solution of sodium hydrogencarbonate and water and thereafter dried with sodium sulfate.

After removing the solvent by distillation, the residue was subjected to a silica gel column chromatography process [silica gel 1 g, solvent; n-hexane-ethylacetate (100:5 v/v)] to obtain 100 mg of 3β-O-(t-butyldimethysilyl)-7,8-dihydroxy-7,8-dihydro-1β-methoxycarbonyloxy vitamin D.

IR spectrum: νmax (CHCl$_3$) cm$^{-1}$: 3550, 1740

NMR spectrum: δ: 0.09(6H,S), 0.77(3H,S), 0.87 (9H,d,J=6Hz), 0.90(9H,S), 3.80(3H,S), 3.50–3.90(1H,m), 3.80(3H,S), 4.60–4.90(1H,m), 4.70(1H,d,J=10 Hz), 5.10(2H,brs), 5.65 (1H,d,J=10Hz), mass spectrum (FD)m/e: 606(M$^-$), 605, 589, 572, 549, 531, 513, 473, 455, 448, 380

The reaction formulas are shown below.

-continued

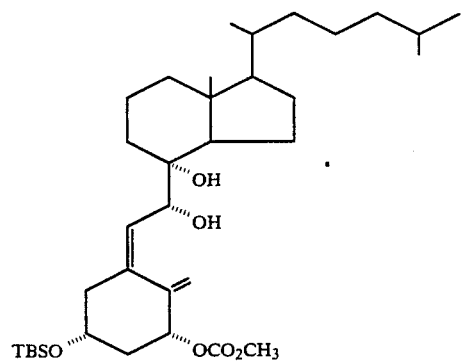

EXAMPLE 6

Preparation of 1β-Methoxycarbonyloxy-3β-O-(t-butyldimethylsilyl) vitamin D

A 90 mg of 3β-O-(t-butyldimethylsilyl)-7,8-dihydroxy-7,8-dihydro-1β-methoxycarbonyloxy vitamin D and 90 mg of triethyl-ortho-formate were dissolved in 20 ml of dry toluene with an amount of pyridinium-para-toluenesulfonate good for catalyst and the solution was heated in a Dean-Stark apparatus for 30 minutes for reflux. After completion of reaction, the solvent was removed by distillation and the residue was subjected to an silica gel column chromatography [silica gel 1 g, solvent; n-hexane-benzene (100:1 v/v)] to obtain 50 mg of 1βmethoxycarbonyloxy3β-O-(t butyldimethylsilyl vitamin D.

IR spectrum: νmax (CHCl$_3$) cm$^{-1}$: 1740

NMR spectrum: (CCl$_4$) δ: 0.09(6H,S), 0.56(3H,S), 0.85 (9H, Hz), 0.90(9H,S), 3.70–4.00(1H,m), 3.80(3H,S), 4.80–5.10(1H,m), 4.90(1H,brs), 5.25(1H,brs), 5.86(1H,d,J=10 Hz), 6.25(1H,d,J=10 Hz)

mass spectrum (FD)m/e: 572(M$^-$), 408, 276

The reaction formulas are shown below.

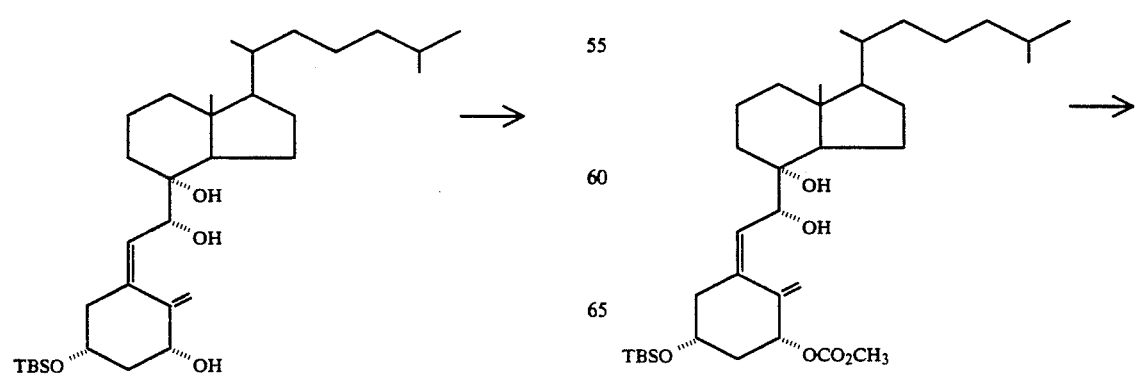

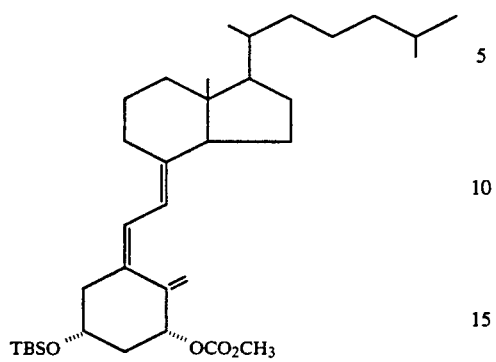
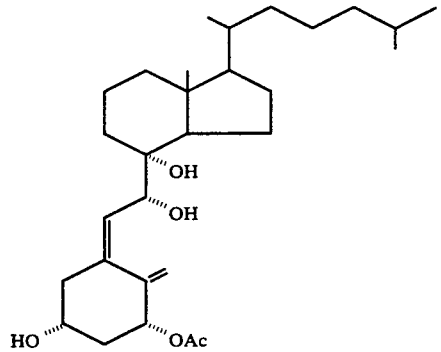

EXAMPLE 7

Preparation of 1-β-acetoxy-7,8-dihydroxy-7,8-hydro vitamin D

A 120 mg of 1β-acetoxy-3β-O-(t-butyldimethylsilyl)-7,8-dihydro vitamin D was dissolved in 1 ml of methanol with an amount of P-toluenesulfonate good for catalyst and the solution was stirred for two hours at room temperature. After completion of reaction, the solvent was removed by distillation and the residue was dissolved in chloroform and washed with saturated aqueous solution of sodium hydrogencarbonate. Again the solvent was removed by distillation and the residue was washed with n-hexane to obtain 100 mmg of β-acetoxy-7,8-dihydroxy-7,8-dihydro vitamin D.

IR spectrum: ν max (CHCl$_3$) cm$^{-1}$: 3550, 1740

NMR spectrum: (CDCl$_3$) δ: 0.77(3H,S), 0.85(9H,d,J=6 Hz), 2.17(3H,S), 3.70–4.10(1H,m), 4.80(1H,d,J=10 Hz), 5.13(1H, brs), 4.90–5.30(1H,m), 5.80(1H,d.J=10 Hz)

mass spectrum (FD)m/e: 476(M−), 459, 416

The reaction formulas are shown below.

EXAMPLE 8

Preparation of 1β-acetoxy-3β-O-acetyl-7,8-dihydroxy-7,8-dihydro vitamin D

A 100 mg of 1β-acetoxy-7,8-dihydroxy-7,8-dihydro vitamin D was dissolved in a mixture of 2 ml of pyridine and 5 ml of methylenechloride and 26 mg of acetic anhydride was dropped into the solution, which was then stirred for 30 minutes at room temperature. After completion of reaction, the solution was diluted with 10 ml of methylenechloride and washed sequentially with 10% hydrochloric acid, water, saturated aqueous solution of sodium hydrogencarbonate and water. The solution was dried with sodium sulfate and the solvent was removed by distillation. The residue was then subjected to a silica gel column chromatography process [silica gel 1 g, solvent; n-hexane-ethylacetate (10:2 v/v)] to obtain 100 mg of 1β-acetoxy-3β-O-acetyl-7,8-dihydroxy-7,8-dihydro vitamin D.

IR spectrum: νmax (CHCl$_3$) cm$^{-1}$: 3550, 1740

NMR spectrum: (CCl$_4$) δ: 0.74(3H,S), 0.85(9H,d,J=6 Hz), 1.97 (3H,S), 2.07(3H,S), 4.40–4.90(1H,m), 4.63(1H,d,J=10 Hz), 4.95–5.10(1H,m), 4.98(1H,brs), 5.03(1H,brs), 5.65(1H,d,J=10 Hz)

mass spectrum (FD)m/e: 518(M−), 501, 458, 265

The reaction formulas are shown below.

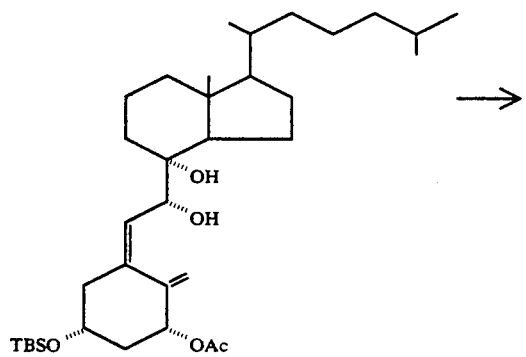
→

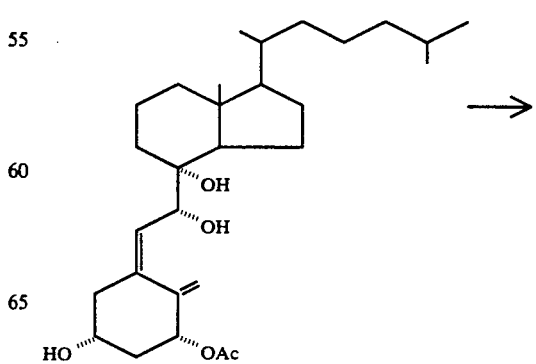
→

-continued

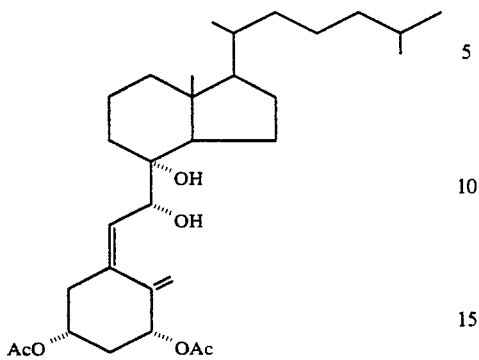

EXAMPLE 9

Preparation of 1β-acetoxy-3β-O-acetyl vitamin D

A 90 mg of 1β-acetoxy-3β-O-acetyl-7,8-dihydroxy-7,8-dihydro vitamin D was dissolved in 20 ml of dry toluene and an amount of pyridinium-para-toluenesulfonate good for catalyst was added to the solution while it was being stirred. The solution was then heated in a Dean-Stark apparatus for 30 minutes for reflux. After completion of reaction, the solvent was removed by distillation and the residue was subjected to a silica gel column chromatography process [silica gel 1 g, solvent; n-hexane-benzene (2:3 v/v)] to obtain 70 mg of 1β-acetoxy-3β-O-acetyl vitamin D.

IR spectrum: $\nu$max (CHCl$_3$) cm$^{-1}$: 1730

NMR spectrum: (CCl$_4$) δ: 0.55(3H,S), 0.90(9H,d,J=6 Hz), 1.95(3H,S), 2.05(3H,S), 4.80–5.00(1H,m), 4.90(1H,m), 4.90 (1H,brs), 5.20(1H,brs), 5.20–5.50(1H,m), 5.90(1H,d,J=10 Hz), 6.30(1H,d,J=10 Hz)

mass spectrum (FD)m/e: 484 (M$^-$), 422, 398

The reaction formulas are shown below.

-continued

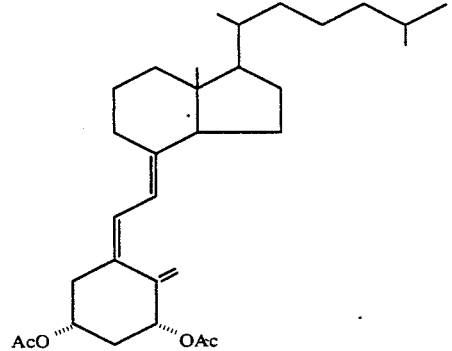

EXAMPLE 10

Preparation of 1β-acetoxy vitamin D

A 100 mg of 1β-acetoxy-3β-O-t-butyldimethylsilyl vitamin D was dissolved into a mixture of 2 ml of methanol and 2 ml of methylenechloride with in the presence of P-toluenesulfonate good for catalyst and the solution was stirred for two hours at room temperature. After completion of reaction, the solution was diluted with 10 ml of methylenechloride and washed sequentially with water, saturated aqueous solution of sodium hydrogencarbonate and water. Then the diluted solution was washed with sodium sulfonate and the solvent was removed by distillation. Thereafter, the residue was subjected to a silica gel column chromatography process [silica gel 1 g, solvent; n-hexane-ethylacetate (100:5 v/v)] to obtain 90 mg of 1β-acetoxy vitamin D.

IR spectrum: $\nu$ max (CHCl$_3$) cm$^{-1}$: 1730

UV λ max (EtOH)nm: 264, 244

NMR spectrum: (CDCl$_3$) δ: 0.53(3H,S), 0.87(9H,d,J=6 Hz), 2.07(3H,S), 3.70–4.20(1H,m), 5.0(1H,brs), 5.27(1H,brs), 5.20–5.50(1H,m), 5.90(1H,d,J=11 Hz), 6.37(1H,d,J=11 Hz)

mass spectrum (FD)m/e: 442(M$^-$), 383

The reaction formulas are shown below.

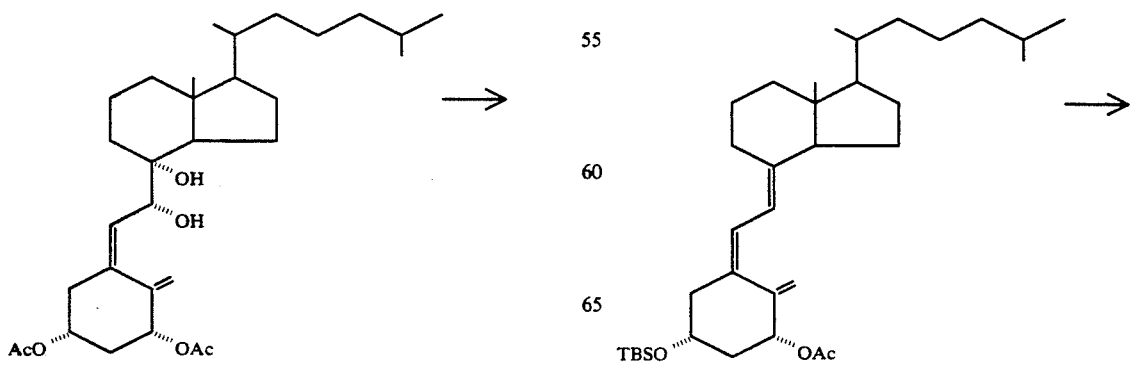

-continued

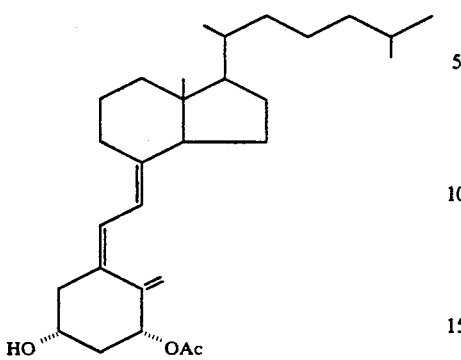

EXAMPLE 11

Preparation of 1β-benzoyloxy vitamin D

A 80 mg of 1β-benzoyloxy-3β-O-t-butyldimethylsilyl vitamin D was dissolved in a mixture of 2 ml of methanol and 2 ml of methylenechloride with in the presence of P-toluenesulfonate good for catalyst and the solution was stirred for two hours at room temperature. After completion of reaction, the solution was diluted with 10 ml of methylenechloride and washed sequentially with water, saturated aqueous solution of sodium hydrogencarbonate and water. Thereafter, the solvent was removed by distillation and the residue was subjected to a silica gel column chromatography process [silica gel 1 g, solvent; n-hexane-ethylacetate (10:1 v/v)] to obtain 50 mg of 1β-benzoyloxy vitamin D.

IR spectrum: $\nu$ max (CHCl$_3$) cm$^{-1}$: 1720

NMR spectrum: (CCl$_4$) δ: 0.53(3H,S), 0.86(9H,d,J=6 Hz), 3.70–4.60(1H,m), 5.00(1H,brs), 5.38(1H,brs), 5.40–5.70 (1H,m), 5.87(1H,d,J=12 Hz), 6.36(1H,d,J=12 Hz), 7.30–7.60 (3H,m), 7.90–8.20 (2H,m)

mass spectrum (FD)m/e: 504(M−), 382, 264

The reaction formulas are shown below.

-continued

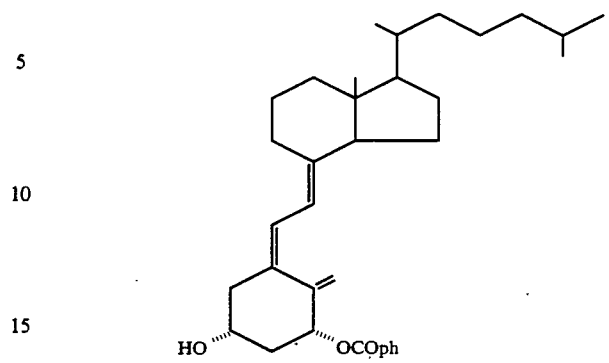

EXAMPLE 12

Preparation of 1β-hydroxy vitamin D

A 28 mg of 1β-acetoxy vitamin D was dissolved in 2 ml of methanol, to which 0.1 ml of caustic soda containing 10% methanol was added. The solution was then stirred for one hour at room temperature and, after completion of reaction, diluted with 10 ml of methylenechloride. Thereafter, the solution was washed with water and dried with potassium carbonate anhydride. After the solvent was removed, the residue was subjected to a silica gel column chromatography process [silica gel 1 g, solvent; n-hexane-ethylacetate (1:1 v/v)] to obtain 20 mg of 1β-hydroxy vitamin D.

A 30 mg of 1β-hydroxy vitamin was obtained from 40 mg of 1β-benzoyloxy vitamin D following a similar process.

IR spectrum: $\nu$max (CHCl$_3$) cm$^{-1}$: 3500

UV $\nu$max (EtOH)nm: 264, 244

NMR spectrum: (CDCl$_3$) δ: 0.57(3H,S), 0.90(9H,d,J=6 Hz), 3.85–4.20(1H,m), 4.20–4.50(1H,m), 5.00(1H,brs), 5.30(1H,brs), 6.05(1H,d,J=10 Hz), 6.47(1H,d,J=10 Hz)

mass spectrum (FD)m/e: 400(M−), 382, 364

The reaction formulas are shown below.

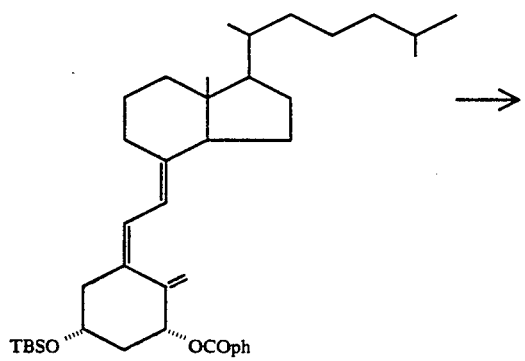

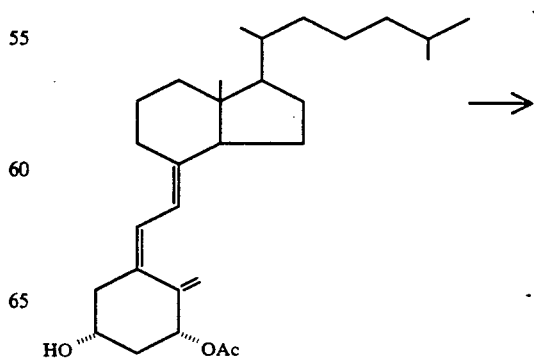

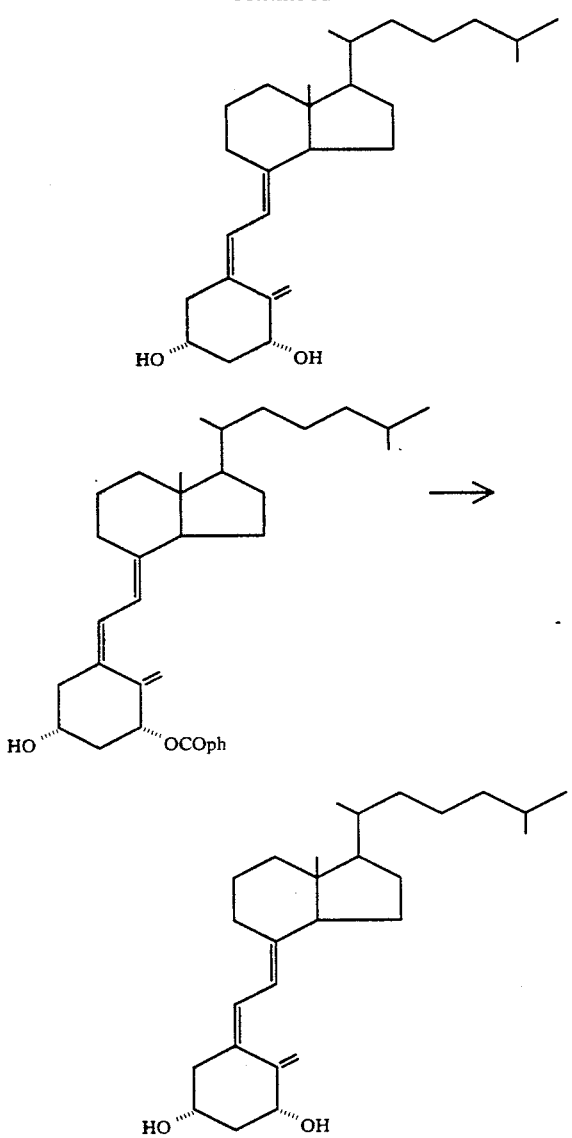

While a variety of 1β-hydroxy vitamin D derivatives were synthesized by using various 7,8-dihydroxy-7,8-dihydro vitamin D derivatives in the above twelve examples, 1α-hydroxy vitamin D derivatives were synthetically prepared from 1β-hydroxy vitamin D derivatives in the following examples.

EXAMPLE 13

Preparation of 3β-(t-butyldimethylsilyl)-1β-hydroxy vitamin D

A 300 mg of 1β-benzoyloxy-3β-O-t-butyldimethylsilyl vitamin D were dissolved in a mixture of 2 ml of methanol and 2 ml of methylenechloride, to which caustic soda solution containing methanol by 10% was added. The solution was stirred for 30 minutes at room temperature and, after completion of reaction, diluted with 20 ml of methylenechloride. Then, the diluted solution was washed with water and dried with potassium carbonate anhydride. Thereafter, the solvent was removed by distillation and the residue was subjected to a silica gel column chromatography process [silica gel 5 g, solvent; n-hexane-ethylacetate (100:1 v/v)] to obtain 227 mg of 3β-O-(t-butyldimethylsilyl)-1β-hydroxy vitamin D.

IR spectrum: ν max (CHCl₃) cm⁻¹: 3450
NMR spectrum: (CCl₄) δ: 0.10(6H,S), 0.55(3H,S), 0.86(9H, d,J=6 Hz), 0.90(9H,S), 3.86–4.20(2H,m), 4.80(1H,brs), 5.15(1H,brs), 5.85(1H,d,J=12 Hz), 6.15(1H,d,J=12 Hz)
mass spectrum (FD)m/e: 514(M⁻), 496

The reaction formulas are shown below.

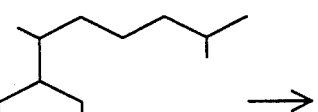

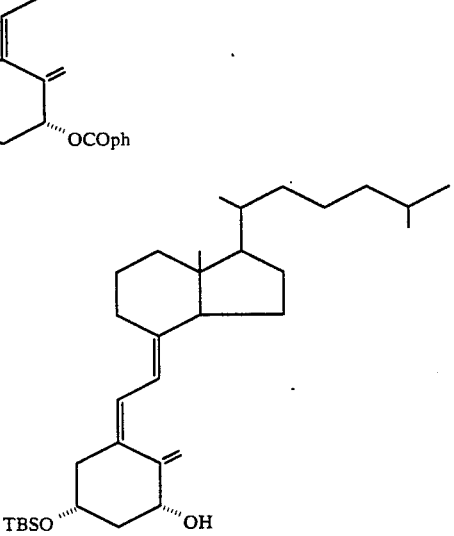

EXAMPLE 14

Preparation of 1α-benzoyloxy-3β-O-t-butyldimethylsilyl vitamin D

A 93 mg of 3β-O-(t-butyldimethylsilyl)-1β-hydroxy vitamin D, 56.9 mg of triphenylphosphine and 26.5 mg of benzoic acid were dissolved in 2 ml of benzene anhydride, to which 37.8 mg of diethyl-azo-dicarboxynate was added. The solution was stirred for three hours at room temperature and, after completion of reaction, diluted with 10 ml of benzene. Thereafter, it was washed sequentially with 10% hydrochloric acid, water, saturated aqueous solution of sodium hydrogencarbonate and water and dried with sodium sulfate. The solvent was removed by distillation and the residiue was subjected to a silica gel column chromatography process [silica gel 1 g, solvent; n-hexane-acetic acid (100:1 v/v)] to obtain 1α-benzoyloxy-3β-O-t-butylmethylsilyl vitamin D.

IR spectrum: ν max (CHCl₃) cm⁻': 1710
NMR spectrum (CCl₄) δ: 0.10(6H,S), 0.30(3H,S), 0.86(9h,d, J=6 Hz), 0.90(9H,S), 3.90–4.20(1H,m), 5.00(1H,brs), 5.35 (1H,brs), 5.40–5.70(1H,m), 5.40(1H,d,J=12 Hz), 6.23(1H,d, J=12 Hz), 7.10–7.45(3H,m)), 7.70–8.00(2H,m) mass spectrum (FD)m/e: 618(M⁻), 593, 578, 562, 547, 528, 512, 483, 464, 436

The reaction formulas are shown below.

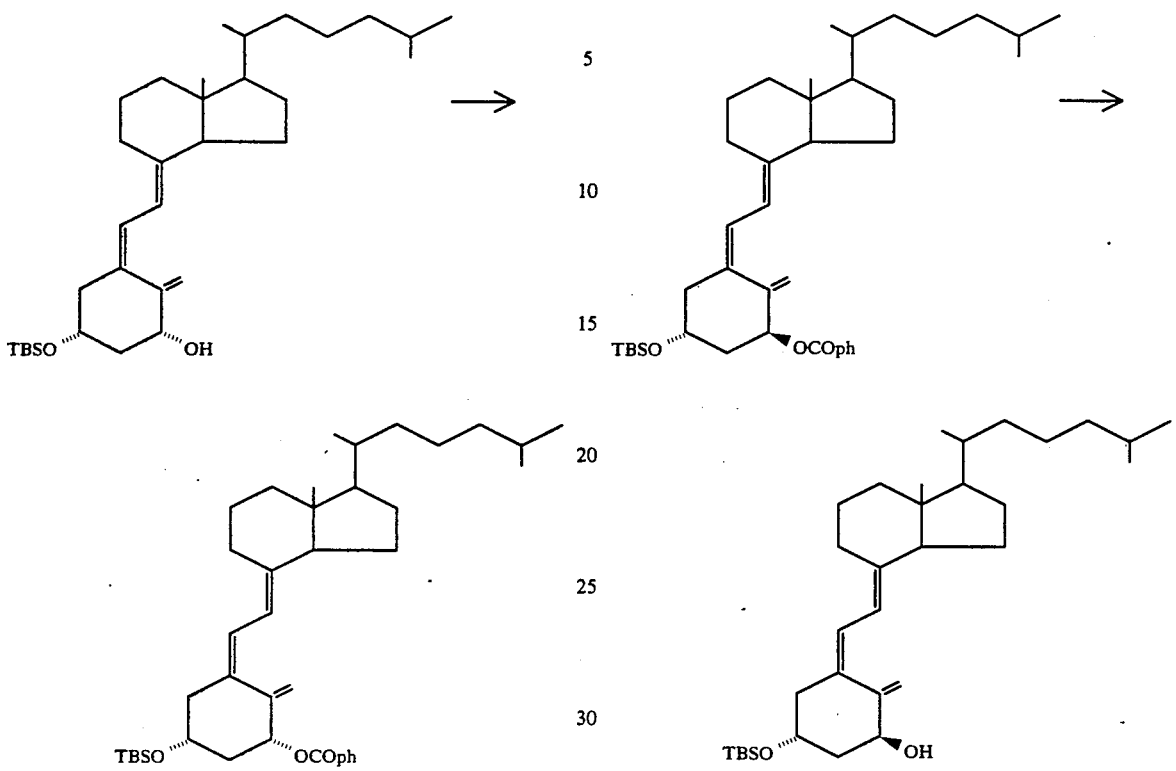

EXAMPLE 15

Preparation of 3β-O-(t-butyldimethylsilyl)-1α-hydroxy vitamin D

A 30 mg of 1α-benzoyloxy-3β-O-t-butyldimethylsilyl vitamin D was dissolved in a mixture of 1 ml of methanol and 10 ml of methylenechloride, to which 0.1 ml of caustic soda containg methanol by 10% was added. The solution was heated and stirred for one hour. After completion of reaction, the solution was diluted with 20 ml of methylenechloride and washed with water. Thereafter, it was dried with potassium carbonate anhydride and the solvent was removed by distillation. Then the residue was subjected to a silica gel column chromatography process [silica gel 1 g, solvent; n-hexane-ethylacetate (100:5 v/v)] to obtain 25 mg of 3β-O-(t-butyldimethylsilyl)-1α-hydroxy vitamin D.

IR spectrum: νmax (CHCl4) cm$^{-1}$: 3550

NMR spectrum: (CCl4) δ: 0.07(6H,S), 0,.55(3H,S), 0.87 (9H,d,J=6 Hz), 0.90(9H,S), 3.90–4.50(2H,m), 4.86(1H,brs), 5.17(1H,brs), 5.84(1H,d,J=12 Hz), 6.17(1H,d,J=12 Hz)

mass spectrum (FD)m/e: 514(M$^-$)

The reaction formulas are shown below.

EXAMPLE 16

Preparation of 1α-hydroxy vitamin D

A 30 mg of 3β-O-(t-butylmethylsilyl)-1α-hydroxy vitamin D was dissolved into 10 ml of tetrahydrofuran anhydride, to which 0.1 ml of tetra-n-butylammoniumfluoride containing 1 mol of tetrahydrofuran was added. The solution was heated and stirred for one hour. After completion of reaction, the solvent was removed by distillation and the residue was washed with water. Thereafter, it was dried with potassium carbonate anhydride and the solvent was further removed by distillation. The residue was subjected to a silica gel column chromatography process [silica gel 1 g, solvent; benzene-ethylacetate (3:2 v/v)] to obtain 23 g of 1α-hydroxy vitamin D.

m.p. 139°–140° C., Colorless Needles (from petroleum ether)

IR spectrum ν max (CHCl3) cm$^{-1}$:3600

UV ν max (EtOH)nm: 264, 244

NMR spectrum: (CDCl3) δ: 0.57(3H,S), 0.92(9H,S), 0.92(9H, d,J=6 Hz), 4.00–4.60(2H,m), 5.02(1H,brs), 5.34(1H,brs), 6.02(1H,d,J=12 Hz), 6.42(1H,d,J=12 Hz)

mass spectrum (FD)m/e: 400(M$^-$)

The reaction formulas are shown below.

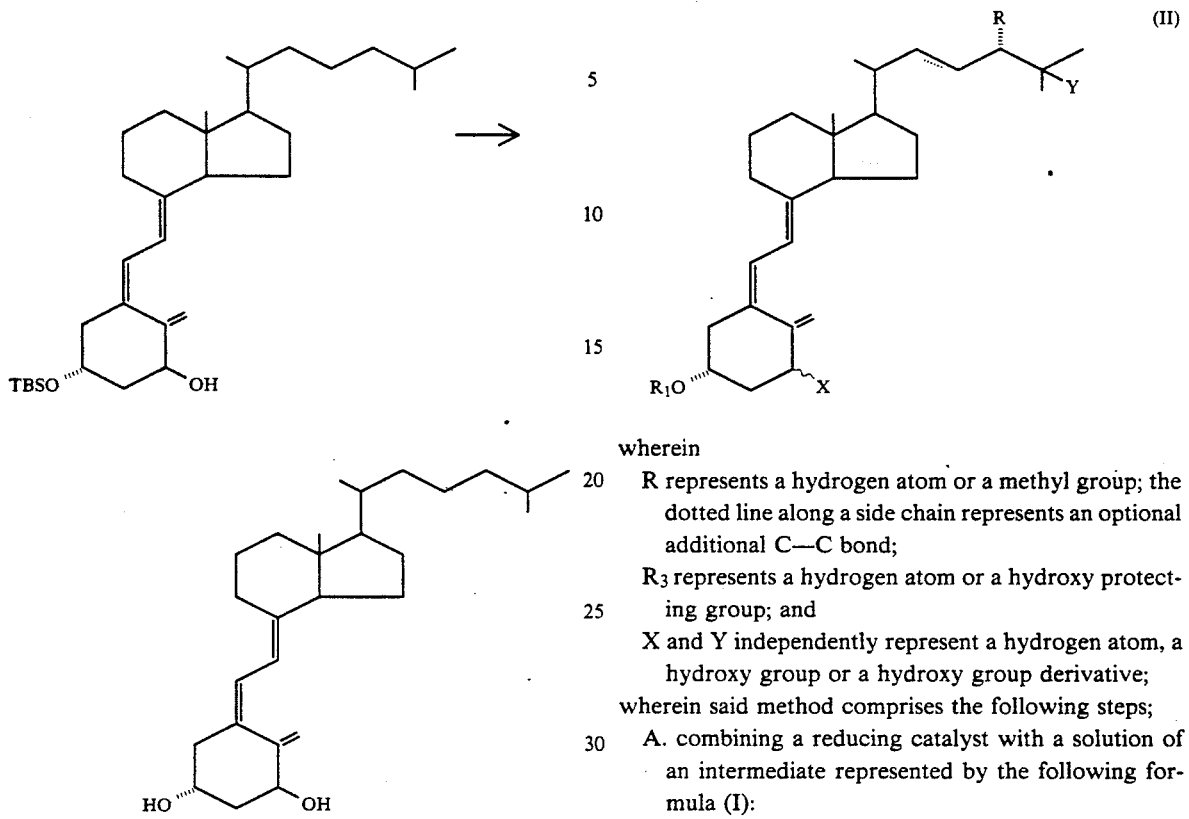

The above described Examples 13 through 16 are examples of variations of 1α-hydroxy vitamin D obtained from various 1β-hydroxy vitamin D derivatives.

POTENTIAL INDUSTRIAL APPLICATIONS

As described above, the present invention provides a method with which vitamin $D_2$, vitamin $D_3$, activated type vitamin $D_2$, activated type vitamin $D_3$ and their derivatives are prepared from 7,8-dihydroxy vitamin $D_2$, $D_3$ or their derivatives by means of a reducing elimination technique involving a cyclic orthoester of a 7,8-dihydroxy compound or a thiocarbonate compound as an intermediate compound or an elimination technique utilizing a reducing metal such as titanium. The method according to the invention ensures a practical and simple synthetic process and a high yield as compared with any existing methods for manufacturing these chemicals.

What is claimed is;

1. A method of manufactoring a derivative of vitamin D represented by the following formula (II):

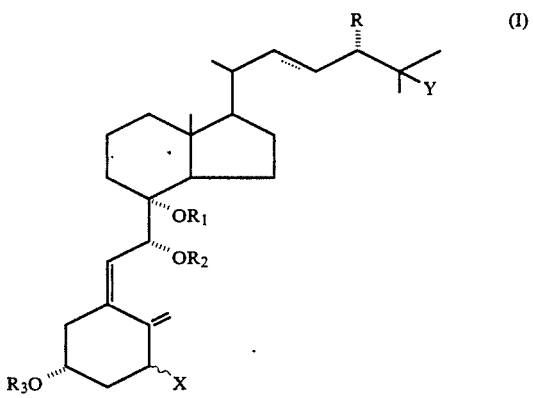

wherein

R represents a hydrogen atom or a methyl group; the dotted line along a side chain represents an optional additional C—C bond;

$R_3$ represents a hydrogen atom or a hydroxy protecting group; and

X and Y independently represent a hydrogen atom, a hydroxy group or a hydroxy group derivative;

wherein said method comprises the following steps;

A. combining a reducing catalyst with a solution of an intermediate represented by the following formula (I):

(I)

wherein $R_1$ and $R_2$ independently represent a hydrogen atom or hydroxy protecting group;

B. heating said solution under conditions such that groups —$OR_1$ and —$OR_2$ are eliminated by reduction by way of a cyclic intermediate selected from the group consisting of a cyclic ortho-ester, a homologue of said cyclic ortho-ester and a thiocarbonate derivative of said cyclic ortho-ester; and C. isolating said derivative of vitamin D.

2. The method according to claim 1 wherein said reducing catalyst is selected from the group consisting of camphor sulfonic acid and pyridinium-para-toleuenesulfomat.

3. A method of manufacturing a derivative of vitamin D represented by the following formula (II)

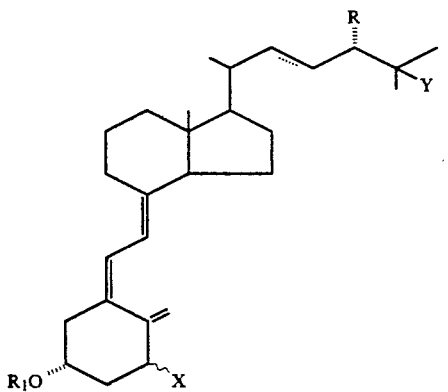

(II)

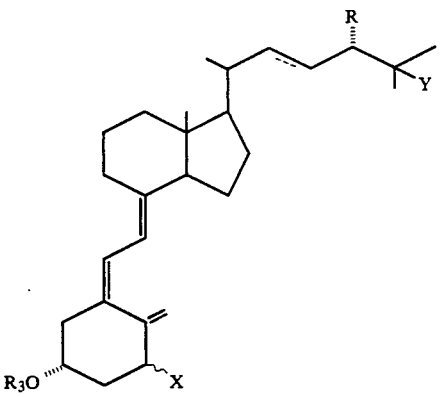

wherein
- R represents a hydrogen atom or a methyl group; the dotted line along a side chain represents an optional additional C—C bond;
- $R_3$ represents a hydrogen atom or a hydroxy protecting group; and
- X and Y independently represent a hydrogen atom, a hydroxy group or a hydroxy group derivative;

wherein said method comprises the following steps:
A. combining a reducing metal with a solution of an intermediate represented by the following formula (I)

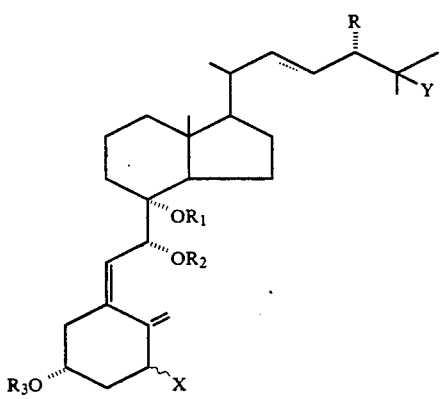

(I)

wherein $R_1$ and $R_2$ independently represent a hydrogen atom or hydroxy protecting group;

B. maintaining said solution under conditions such that groups —$OR_1$ and —$OR_2$ are eliminated by reduction by way of a cyclic intermediate selected from the group consisting of a cyclic ortho-ester, a homologue of said cyclic ortho-ester and a thiocarbonate derivative of said cyclic ortho-ester; and C. isolating said derivative of vitamin D.

4. The method according to claim 3 wherein said reducing metal is titanium.

5. The method according to claim 3 wherein said reducing catalyst is dissolved in toluene containing triethylorthoformate.

6. A method of manufacturing a derivative of vitamin D represented by the following formula (II):

wherein
- R represents a hydrogen atom or a methyl group; the dotted line along a side chain represents an optional additional C—C bond;
- $R_3$ represents a hydrogen atom or a hydroxy protecting group; and
- X and Y independently represent a hydrogen atom, a hydroxy group or a hydroxy group derivative;

wherein said method comprises the following steps:
A. combining camphor sulfonic acid and triethylorthoformate with a solution of an intermediate represented by the following formula (I):

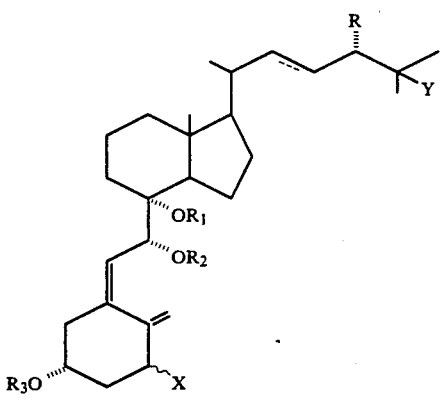

wherein $R_1$ and $R_2$ independently represent a hydrogen atom or hydroxy protecting group;

B. heating said solution under conditions such that group —$OR_1$ and —$OR_2$ are eliminated by reduction by way of a cyclic intermediate selected from the group consisting of a cyclic ortho-ester, a homologue of said cyclic ortho-ester and a thiocarbonate derivative of said cyclic ortho-ester; and C. isolating said derivative of vitamin D.

7. A method of manufacturing a derivative of vitamin D represented by the following formula (II):

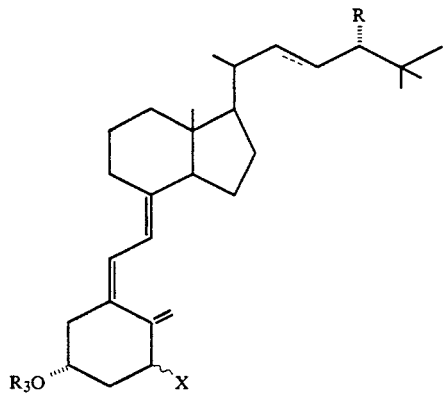

wherein
R represents a hydrogen atom or a methyl group; the dotted line along a side chain represents an optional additional C—C bond;

$R_3$ represents a hydrogen atom or a hydroxy protecting group; and

X and Y independently represent a hydrogen atom, a hydroxy group or a hydroxy group derivative;

wherein said method comprises the following steps:

A. combining pyridinium-para-toluenesulfonate with a solution of an intermediate represented by the following formula (I):

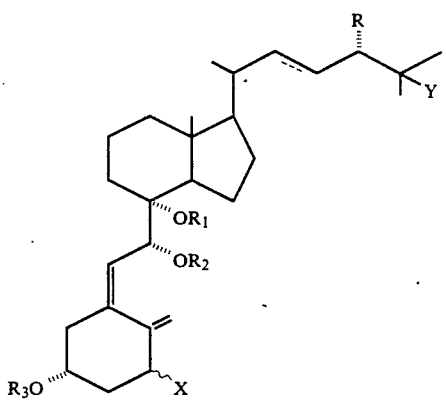

wherein $R_1$ and $R_2$ independently represent a hydrogen atom or hydroxy protecting group;

B. heating said solution under conditions such that groups —$OR_1$ and —$OR_2$ are eliminated by reduction by way of a cyclic intermediate selected from the group consisting of a cyclic ortho-ester, a homologue of said cyclic ortho-ester and a thiocarbonate derivative of said cyclic ortho-ester; and C. isolating said derivative of vitamin D.

* * * * *